United States Patent
Kimata

(10) Patent No.: US 7,193,213 B2
(45) Date of Patent: Mar. 20, 2007

(54) METHOD FOR MEASUREMENT OF SILANOL GROUP CONCENTRATION AND CELL FOR MEASUREMENT

(75) Inventor: Yoshinori Kimata, Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 129 days.

(21) Appl. No.: 10/523,597

(22) PCT Filed: Aug. 8, 2003

(86) PCT No.: PCT/JP03/10124

§ 371 (c)(1),
(2), (4) Date: Feb. 4, 2005

(87) PCT Pub. No.: WO2004/015401

PCT Pub. Date: Feb. 19, 2004

(65) Prior Publication Data

US 2006/0118723 A1    Jun. 8, 2006

(30) Foreign Application Priority Data

Aug. 9, 2002  (JP) .............................. 2002-233192

(51) Int. Cl.
*G01J 3/02* (2006.01)
(52) U.S. Cl. ................................. 250/339.12
(58) Field of Classification Search ............ 250/339.12
See application file for complete search history.

(56) References Cited

U.S. PATENT DOCUMENTS 3,886,364 A * 5/1975 Walker et al. ............... 250/343

FOREIGN PATENT DOCUMENTS

| JP | 5 52743 A | 3/1993 |
| JP | 07-209158 | 8/1995 |
| JP | 09-318525 | 12/1997 |

(Continued)

OTHER PUBLICATIONS

Fang, C.S. et al., Equipment for High-Pressure Infrared Measurements, Applied Spectroscopy, vol. 24, No. 1, 1970, pp. 21-27.*

*Primary Examiner*—David Porta
*Assistant Examiner*—Mark R. Gaworecki
(74) *Attorney, Agent, or Firm*—Norris McLaughlin & Marcus PA

(57) ABSTRACT

The removal of intra-cell moisture can be performed within a short period of time by the use of pressure cell. In particular, a method of measuring the concentration of silanol groups characterized in that in the measurement of the concentration of silanol groups in a silicon compound according to infrared absorption spectroscopy, a step of maintaining an intra-cell pressure at 20 Pa or below and a step of maintaining the same at 0.2 to 1 MPa are repeated at least twice before charging the cell with a silicon compound, thereafter a silicon compound is introduced in the cell and cell for measurement thereof is carried out to thereby identify the concentration of silanol groups in the silicon compound. For this method, there is provided a cell for infrared absorption spectroscopy measurement thereof is carried out to thereby identify the concentration of silanol groups in the silicon compound. For this method, there is provided a cell for infrared absorption spectroscopy measurement which can withstand a vacuum of 20 Pa or below and also can withstand a pressurization of 0.2 to 1 MPa.

3 Claims, 4 Drawing Sheets

FOREIGN PATENT DOCUMENTS

| | | |
|---|---|---|
| JP | 10-176988 | 6/1998 |
| JP | 11-183366 | 7/1999 |
| JP | 2000-210550 | 8/2000 |
| JP | 2001-108610 | 4/2001 |
| JP | 2001-208683 | 8/2001 |
| JP | 2002-022648 | 1/2002 |
| JP | 2002-071551 | 3/2002 |
| JP | 2003-035667 | 2/2003 |
| WO | WO 97/14951 | 4/1997 |

* cited by examiner

METHOD FOR MEASUREMENT OF SILANOL GROUP CONCENTRATION AND CELL FOR MEASUREMENT

TECHNICAL FIELD

Silicon halide compounds such as silicon tetrachloride and the like are highly reactive with water and react easily with a very small amount of water in the air to form hydrogen chloride gas and a silanol group. In the present invention, infrared absorption spectrum is utilized for quantitative determination of a very small amount of silanol group contained in a silicon compound. Further, in the present invention, a pressure-resistant cell for measurement of infrared absorption spectrum is used, enabling a rapid and highly accurate measurement of silanol group concentration.

BACKGROUND ART

Silicon halide compounds suitably used as a material for formation of silicon nitride film, undergo hydrolysis by mere contact with a slight amount of water vapor contained in the air, to form hydrogen chloride gas and a silanol group. It is known that the thus-formed silanol group gives an adverse effect on the property of the silicon nitride film formed from a silicon halide compound. Therefore, it is necessary to quantitatively determine the silanol group of a silicon halide compound for quality control of the compound.

In order to quantitatively determine a very small amount of the silanol group present in a silicon compound, infrared spectrophotometry is known. For example, in JP-A-9-318525 is described an infrared spectrophotometry wherein an optical path length, i.e. a length of sample layer through which an infrared light is transmitted, is set at 50 to 150 mm in order to measure a silanol group of about 0.1 ppm. In the method for measurement of silanol group, described in the literature, there is used a cell constituted by a stainless steel-made cylinder and infrared-transmitting, calcium fluoride-made windows fitted to the cylinder.

In order to measure a silanol group of a very small amount, for example, 0.1 ppm or less, it is generally necessary to remove a very small amount of the water adhering to a cell to be used for measurement and then place a sample into the cell. It is because, when a sample is placed in a cell of insufficient water removal and is measured for the concentration of silanol group, the residual water in the cell and silicon halide compound react with each other to form a silanol group, which is included in the measurement data obtained, as an error. Hence, in the method for measurement of silanol group, described in the JP-A-9-318525, it was necessary to beforehand pass a large amount of nitrogen gas of water content of 0.5 ppm or less, through the cell inside, or, in addition with the passing of the above mentioned nitrogen gas, to clean the cell inside with the sample per se. When the sample is a silicon halide of low volatility, such as hexachlorodisilane or the like, the above-mentioned cell cleaning has had to be conducted taking a very long time when a new sample is filled in the cell in place of the used sample.

As described above, with the conventional method, much time and labor have been required for the removal of water from cell inside, making difficult the rapid measurement of a very small amount of silanol group.

The present invention is intended to provide a method which can measure a silanol group of very small amount (0.05 to 0.1 ppm level) rapidly and easily, and a cell for measurement of infrared absorption spectrum, used in the method.

DISCLOSURE OF THE INVENTION

The present inventors made a study in order to achieve the above-mentioned tasks. As a result, by using a cell for measurement of infrared absorption spectrum, which can withstand a reduced pressure and also an applied pressure, and repeatedly conducting pressure reduction of cell inside and pressure application of cell inside using a dry inert gas, water removal from cell inside has been made possible in very short time.

The first aspect of the present invention lies in:

a method for measurement of silanol group concentration in silicon compound by infrared spectrophotometry, which comprises:

conducting, prior to filling of a silicon compound in a cell, at least twice each of a step of keeping the cell inside at 20 Pa or lower and a step of keeping the cell inside at 0.2 to 1 MPa, then, introducing the silicon compound into the cell and measuring the infrared absorption spectrum thereof, to measure the concentration of the silanol group in the silicon compound.

The second aspect of the present invention lies in:

a cell used for measurement of infrared absorption spectrum, which can withstand a reduced pressure of 20 Pa or lower and a pressure of 0.2 to 1 MPa. Incidentally, Pa and MPa are each a pressure unit and mean Pascal and mega Pascal, respectively. They are in a relation of 1 MPa=$10^6$ Pa.

The present invention is described in detail below.

Figure 1:
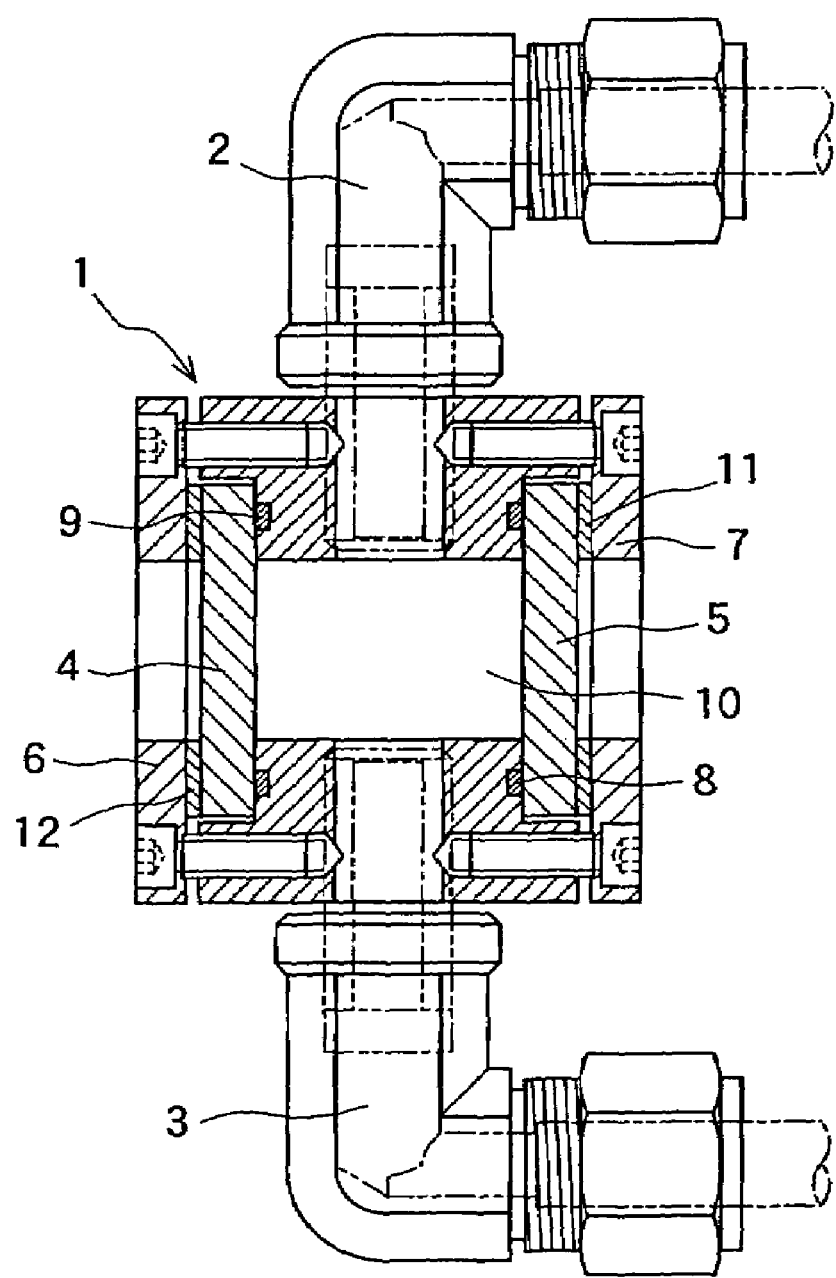
FIG. 1 is a vertical sectional view showing an example of the cell for measurement of infrared absorption spectrum (this cell is hereinafter referred to simply as cell), used in the present invention.
Figure 2:
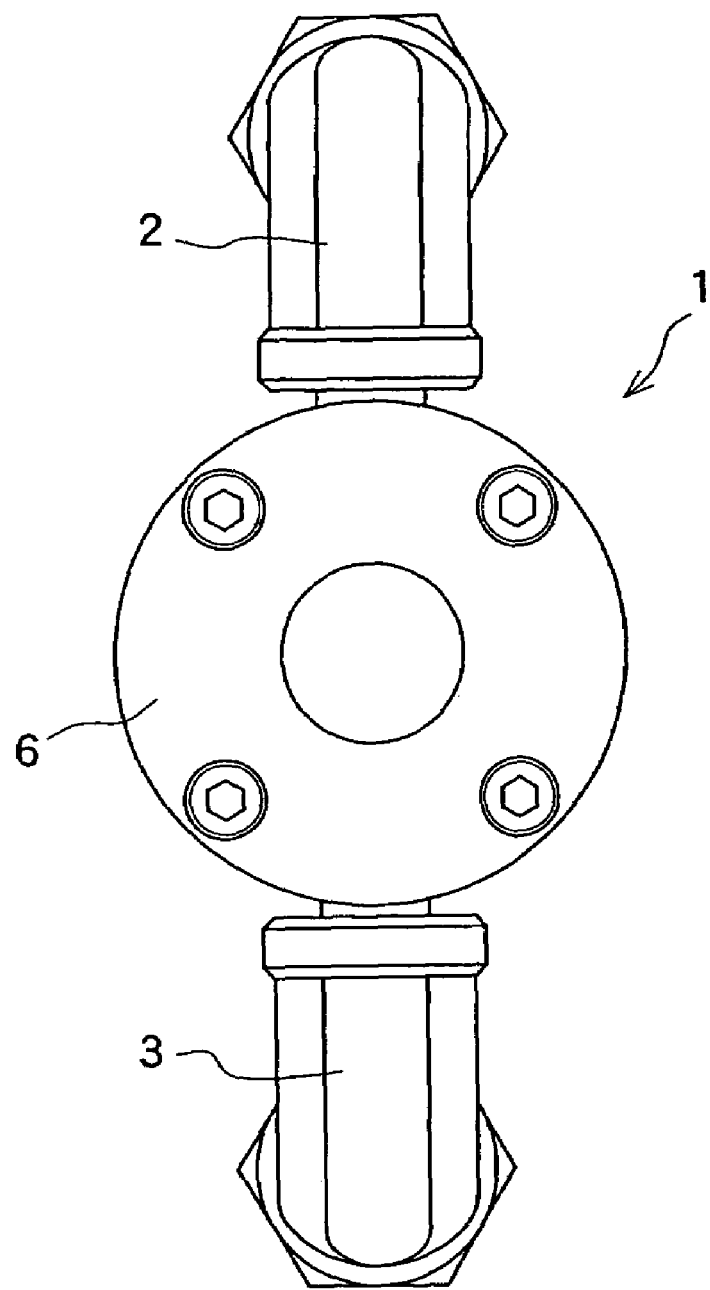
FIG. 2 is a front view of the cell of FIG. 1.
Figure 3:
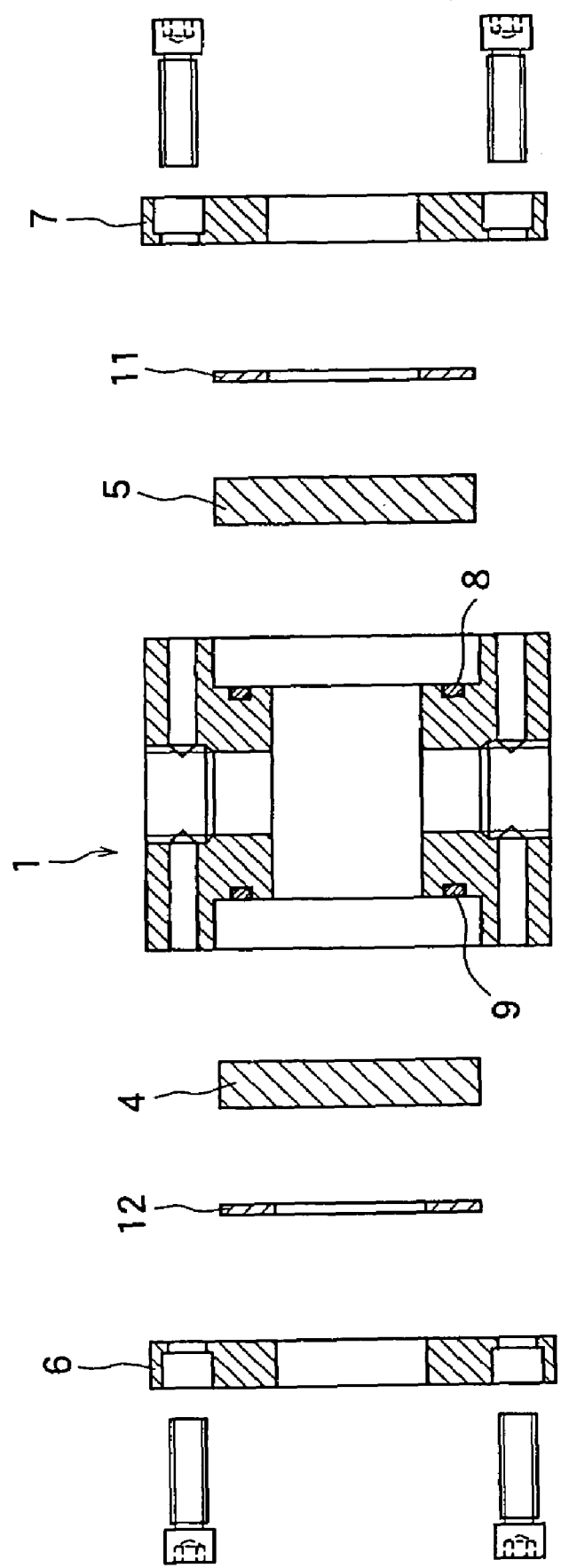
FIG. 3 shows vertical sectional views of the parts obtained by disassembling the cell of FIG. 1.

Explanation of the Symbols Used in FIG. 1 to FIG. 3
1: Cell trunk (hereinafter referred to simply as trunk)
2: Pipe for connection to vacuum system
3: Pipe for connection to sample system
4,5: Infrared-transmitting window panels
6,7: Holders for window panel
8,9: O-rings
10: Sample space
11,12: Gaskets Explanation of the Symbols Used in FIG. 4
13: Cell
14: Container for sample
15: Container for recovered sample
16: Vacuum gauge
17: Nitrogen gas
18: Vacuum pump ahead of the arrow

BEST MODE FOR CARRYING OUT THE INVENTION

Figure 4:
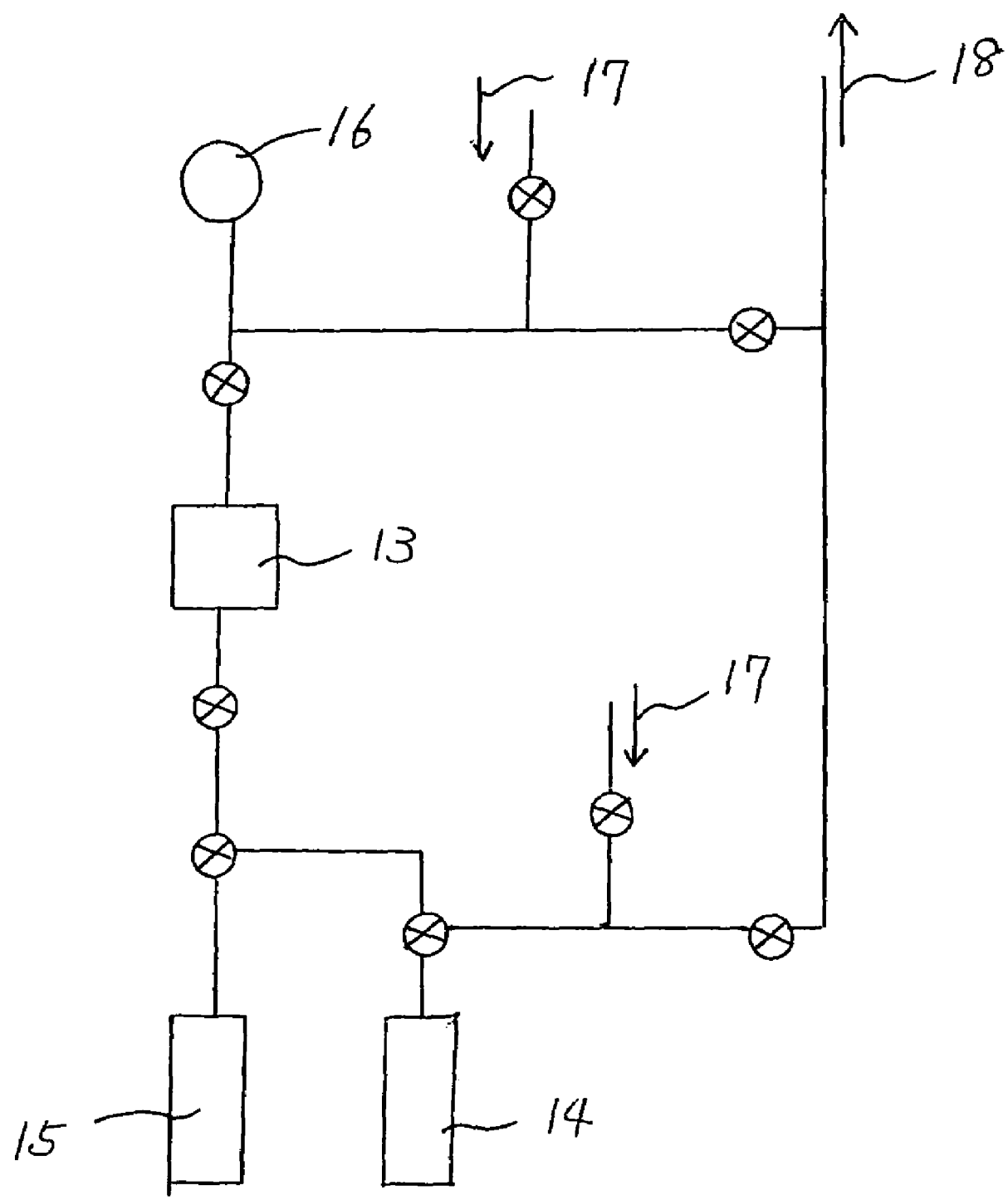
FIG. 4 is a conceptual view indicating the connections between a cell and pipes running in the vicinity of the cell, which are necessary for feeding a sample into the cell.

In a cell shown in FIGS. 1 to 3, a trunk 1 has a cylindrical or rectangular prism shape and can transmit an infrared light in the axial direction. The trunk 1 has one pair of openings at the top and bottom of the central portion of the cylindrical or rectangular prism shape, and is connected, at these openings, to a pipe 2 and a pipe 3. As shown in FIG. 4, the pipe 2 present above the cell is connected to an outside vacuum system and the pipe 3 present below the cell is connected to an outside sample system.

At the both ends of the trunk 1 of cylindrical or rectangular prism shape are fixed window panels 4 and 5 each made of a material superior in infrared transmittance. As shown in FIG. 1 and FIG. 2, O-rings 8 and 9 are placed between the window panels 4 and 5 and the trunk 1; gaskets 11 and 12 are placed between the window panels 4 and 5 and window panel holders 6 and 7; in this state, the window panel holders 6 and 7 are tightened using bolts, whereby the window panels 4 and 5 are fixed to the trunk 1. As is clear also from FIG. 2, the central portion of the window panel holders 6 and 7 are made into a hole so as to allow passing of an infrared light therethrough. Preferred shape of the trunk 1 is cylindrical, because the shape can withstand a high pressure.

A liquid sample is filled in a space 10 formed by the trunk 1 and the infrared-transmitting window panels 4 and 5; and an infrared light coming into the space 10 from one window panel, passes through the liquid sample, leaves the space 10 from other window panel, and reaches an infrared light detection section. The distance sandwiched by the window panels 4 and 5, i.e. the length in which an infrared light enters the liquid sample and leaves it, is called optical path length. The preferred optical path length changes depending upon the concentration of silanol groups in silicon compounds to be measured. A large optical path length enables measurement of a silanol group of low concentration, however reduces the strength of cell structure.

As described previously, the present invention aims at measurement of silanol group of 0.05 to 0.1 ppm level. Further in the present invention, rapid measurement of silanol group is made possible by using a pressure-resistant cell. In view of the balance between silanol group concentration and the pressure resistance of cell, the optical path length is preferred to be 5 to 40 mm. Two thin window panels 4 and 5 are inferior in pressure resistance and the thickness of the window panels 4 and 5 are preferred to be 2 to 8 mm. The window diameter is preferred to be 5 to 20 mm.

The material constituting the trunk 1 is preferably Hastelloy or stainless steel because they are superior in corrosion resistance to silicon compounds, hydrogen chloride, etc. The base material used for the infrared-transmitting window panels 4 and 5 may be a material which can transmit an infrared light of 4,000 to 3,000 cm$^{-1}$ at which silanol group is measured, and for example, potassium bromide, potassium chloride, sodium chloride, calcium fluoride, germanium, silicon, zinc selenide, sapphire and quartz can be used. Of these, preferred are germanium, silicon, zinc selenide, sapphire and quartz because they are superior in strength and hardly give rise to breakage; more preferred are zinc selenide, sapphire and quartz. The material for the O-rings 8 and 9 and the gaskets 11 and 12 is preferably, for example, Viton®, Karlez or Teflon®.

In the present invention, in order to remove a very small amount of the water adhering to the inside of a cell, efficiently in a short time, the procedure of once reducing the cell-inside pressure to 20 Pa or lower and then increasing the cell-inside pressure to 0.2 to 1 MPa using a dry inert gas, specifically, for example, nitrogen gas having a water content of 0.1 ppm or less, is repeated at least twice prior to filling a sample into the cell.

The cell of the present invention is connected to a vacuum system and a sample system via a pipe 2 and a pipe 3, as shown in FIG. 4.

Before the sample is fed into the cell, the pressure of the cell inside is reduced to 20 Pa or lower using a vacuum pump, then, a dry inert gas is introduced by pressurization. The pressure for the gas introduction is at least 0.2 MPa, however, the upper limit is 1 MPa because too high a pressure causes cell breakage. By conducting such an operation of pressure reduction and pressurization by inert gas at least twice, preferably at least 5 times, the water in the cell can be removed almost completely.

As the pressure-resistant cell which can withstand the above operation and yet can measure a silanol group of very small amount (0.05 to 0.1 ppm), a cell having an optical path length of 4 to 50 mm and a window diameter of 5 to 20 mm and wherein each window panel has thickness of 2 to 8 mm and the trunk is made of a metal such as stainless steel, Hastelloy or the like can be used, for example. A cell using quartz or sapphire as the material for window panel can withstand a pressure of 3 MPa. By employing a high pressure in the drying operation of the cell inside, the repeating frequency of pressure reduction and pressure application can be reduced.

According to a sample filling system shown in FIG. 4, feeding of the sample into cell can be conducted through a pipe without having sample contact with atmosphere. A liquid sample can be sent into a cell from a sample container via the pipe, by utilizing a pressure difference between the sample container and the inside of the cell. After the sample has been filled in the cell, measurement of infrared absorption spectrum is conducted. After the measurement of infrared absorption spectrum, an inert gas is introduced to discharge the sample from the cell into a sample-collecting container. By conducting the above-mentioned operation of pressure reduction and pressure application by inert gas to the pipe and the cell inside, the sample adhering thereto can be removed; thereby, a state allowing the measurement of next sample is obtained.

Thus, according to the present invention, a very small amount of silanol group can be measured at a high accuracy without using an operation of passing an inert gas for a long time and cleaning the inside of cell with a large amount of a sample. Further in the present invention, since the feeding of sample into cell is conducted in a closed system, there is no need of using a glove box.

The cell of the present invention may be used per se. However, in order to avoid a danger when breakage of window panel has occurred, the cell may be used in a state that the whole cell is covered with a protective case having one pair of windows for infrared transmittance.

The sample to be measured in the present invention is a liquid, organic or inorganic silicon compound, or a silicon compound which is gaseous at ordinary temperature, such as hexachlorodisilane or the like. Such a silicon compound may be a single compound or a mixture. Further, a solid silicon compound soluble in organic solvents, etc. allows for measurement of infrared absorption spectrum when made into a solution; therefore, the solid silicon compound is included in the sample to be measured in the present invention. In the present invention, particularly preferred as the sample to be measured are silicon halides (such as silicon tetrachloride, hexachlorodisilane and the like), alkoxysilanes, etc.

The present invention is described specifically below by way of Examples.

EXAMPLE 1

As a cell for measurement, there was used a cell having a structure of FIG. 1 and the following specification.

Trunk material: Hastelloy® nickel-based corrosion-resistant alloy, trunk size: 40 mm (diameter)×40 mm (outer diameter)

Material for infrared-transmitting window panel: zinc selenide (effective diameter for light receiving: 15 mm)

Optical path length: 2 cm

Pipe: ¼ inch pipe made of SUS 304

Analytical instrument and measurement condition: Nicolet Magna 750 FT-IR spectrometer Infrared spectrometer: detector=DTGS, beam splitter=potassium bromide, resolution=4 cm$^{-1}$, scanning wavelength range=4,000 to 3,000 cm$^{-1}$, accumulation=32 times The cell of the present invention was fitted to the infrared spectrometer. The cell was connected to a vacuum system and a sample system in position relationships shown in FIG. 4. First, the inside of the cell was degassed for about 1 minutes using a vacuum pump until a pressure of 20 Pa or lower was reached; then, a dry nitrogen gas was introduced until a pressure of 0.5 MPa was reached; this operation of degassing and gas-introduction was repeated five times.

In a state that the cell inside was filled with nitrogen gas, a background spectrum was measured. With cell inside being made vacuum again, hexachlorodisilane (a product of Toagosei Co., Ltd.) was introduced into the cell from a sample container via a pipe to carry out the first operation of the spectral measurement.

The hexachlorodisilane sample after measurement was discharged from the cell into a sample-collecting container. In order to remove the sample remaining in the cell and the pipe, degassing was conducted for 10 minutes using the vacuum pump; then, nitrogen gas was introduced until a pressure of 0.5 MPa was reached. Thereafter, 1-minute pressure reduction and pressure application was repeated 5 times. As a result, the remaining sample was removed and the pressure came down to 20 Pa or lower, and, in the same operation as in the first time, hexachlorodisilane was filled in the cell and spectral measurement was made.

In the infrared absorption spectra obtained in the first time and the second time, there were observed, at 3,650 cm$^{-1}$, characteristic absorption peaks of stretching vibration caused by the OH group of silanol group; and their absorbances were 0.0012 and 0.0013, respectively. By comparison with a standard sample (trimethylsilanol) of known concentration, the silanol group concentration of first time and second time were 3.9 μmol/L and 4.2 μmol/L (0.04 ppm in terms of OH group weight).

INDUSTRIAL APPLICABILITY

The method for measurement of silanol group concentration in silicon compound, according to the present invention can be used for quality control of the silicon compounds used in electronic material such as silicon nitride film. Further, the pressure-resistant cell for measurement of infrared absorption spectrum, according to the present invention can be used for measurement of infrared absorption spectra of not only silicon compounds but also of various other compounds, and is most suitable for compressed and liquefied gases.

The invention claimed is:

1. A method for measurement of silanol group concentration in silicon compound by infrared spectrophotometry, which comprises: conducting, prior to filling of a silicon compound in a cell, at least twice each of a step of keeping the cell inside at 20 Pa or lower and a step of keeping the cell inside at 0.2 to 1 MPa, then, introducing the silicon compound into the cell and measuring the infrared absorption spectrum thereof, to measure the concentration of the silanol group in the silicon compound and recording the results.

2. A cell used for measurement of infrared absorption spectrum capable of withstanding a reduced pressure of 20 Pa or lower and a pressure of 0.2 to 1 MPa, comprising a trunk made of stainless steel or nickel-based corrosion-resistant alloy and infrared-transmitting window panels and has an optical path length of 5 to 40 mm, wherein each window panel has a thickness of 2 to 8 mm.

3. A cell used for measurement of infrared absorption spectrum, capable of withstanding an applied pressure of 3 MPa or lower, comprising a trunk made of stainless steel or nickel-based corrosion-resistant alloy and infrared-transmitting window panels made of quartz or sapphire and has an optical path length of 5 to 40 mm, wherein each window panel has a thickness of 2 to 8 mm.

* * * * *